United States Patent
Chen

(10) Patent No.: US 8,413,267 B2
(45) Date of Patent: Apr. 9, 2013

(54) COMBINATION GOGGLE

(75) Inventor: Chih-Ming Chen, Tainan (TW)

(73) Assignee: HWA MEEI Optical Co., Ltd., Tainan (TW)

( * ) Notice: Subject to any disclaimer, the term of this patent is extended or adjusted under 35 U.S.C. 154(b) by 219 days.

(21) Appl. No.: 13/069,478

(22) Filed: Mar. 23, 2011

(65) Prior Publication Data

US 2012/0240315 A1    Sep. 27, 2012

(51) Int. Cl.
*A61F 9/02* (2006.01)

(52) U.S. Cl.
USPC .............................................................. 2/431

(58) Field of Classification Search .................. 2/10, 12, 2/431, 434, 448
See application file for complete search history.

(56) References Cited

U.S. PATENT DOCUMENTS

| 3,931,646 | A  | * | 1/1976  | Loughner ........................ 2/452 |
| 4,455,689 | A  |   | 6/1984  | Boyer |
| 6,907,617 | B2 | * | 6/2005  | Johnson .............................. 2/13 |
| 6,952,841 | B2 | * | 10/2005 | Schary et al. ..................... 2/452 |
| 7,526,813 | B2 | * | 5/2009  | Tominaga et al. .................. 2/13 |
| 8,128,218 | B2 | * | 3/2012  | Stanley et al. .................. 351/47 |
| 2009/0313746 | A1 |   | 12/2009 | Wang |

FOREIGN PATENT DOCUMENTS

| DE | 460229 C | 5/1928 |
| DE | 20306048 U1 | 6/2003 |
| GB | 296945 | 9/1928 |

* cited by examiner

*Primary Examiner* — Katherine Moran
(74) *Attorney, Agent, or Firm* — Alan Kamrath; Kamrath IP Lawfirm, P.A.

(57) ABSTRACT

A combination goggle includes a goggle frame, a lens, and two binding cords for fastening the lens to the goggle frame. The goggle frame includes a positioning groove located in each of two sides thereof. The lens includes an inner surface abutting against an outer face of the goggle frame. The binding cords are bilaterally arranged on the lens, and each binding cord includes first and second ends respectively affixed to the lens and a middle section detachably fastened to one of the positioning grooves of the goggle frame.

7 Claims, 4 Drawing Sheets

COMBINATION GOGGLE

BACKGROUND OF THE INVENTION

1. Field of the Invention

The present invention relates to a combination goggle and, more particularly, to a combination goggle allowing convenient replacement of the lens.

2. Description of the Related Art

When playing an outdoor sport game or activity, such as playing a ball game, riding a bicycle, performing snow skiing, or running on the open field, one may wear a sports goggle or protection goggle to protect the eyes. A goggle for this purpose generally includes a goggle frame, a lens mounted to the goggle frame, and a headband mounted to two sides of the goggle frame for fastening on a user's head. The lens is a single piece member and detachably fastened to the goggle frame. Thus, different types of lenses can be selectively used to fit different application requirements. However, according to the conventional designs, it is inconvenient to mount the lens in the goggle frame or to detach the lens from the goggle frame. Specifically, conventional goggles have the lens and the goggle frame to be fastened together by means of the matching of male fastening means and female fastening means, for example pins and pinholes. However, the tooling cost to make male fastening means and female fastening means on the lens and the goggle frame is high. Any alignment error between the male fastening means and female fastening means will result in a defective product. Further, when the male fastening means and the female fastening means are fastened together, the connection tightness of the male fastening means and the female fastening means may causes the lens dismounting operation difficult. When detaching the lens from the goggle frame, the male fastening means may be broken accidentally, shortening the service life of the goggle.

BRIEF SUMMARY OF THE INVENTION

Thus, an objective of the present invention is to provide a combination goggle, which allows replacement of the lens and facilitates mounting and dismounting of the lens without the use of male and female fastening means, and has the advantages of low manufacturing cost and long service life.

To achieve this and other objectives, a combination goggle of the present invention includes a goggle frame, a lens, and two binding cords for fastening the lens to the goggle frame. The goggle frame includes first and second sides spaced in a width direction and outer and inner faces opposed in a thickness direction perpendicular to the width direction. A positioning groove is provided in each of the first and second sides of the goggle frame. The lens includes outer and inner surfaces opposed in the thickness direction, and the inner surface of the lens faces and abuts against the outer face of the goggle frame. The two binding cords are respectively arranged on two sides of the lens. Each binding cord includes a first end, a second end, and a middle section intermediate the first and second ends. The first and second ends of each binding cord are fixedly fastened to the lens, and the middle section of each binding cord is detachably engaged to one of the positioning grooves of the goggle frame.

In a preferred form, each positioning groove is located between the outer and inner faces of the goggle frame in the thickness direction. The lens further includes upper and lower ends spaced in a vertical direction perpendicular to the width and thickness directions. The two binding cords are arranged on the two sides of the outer surface of the lens, and the first and second ends of each binding cord are respectively fixedly fastened to the upper and lower ends of the outer surface of the lens.

In another preferred form, the lens further includes a rim extending around a periphery thereof. The rim includes upper and lower ends spaced in the vertical direction and outer and inner surfaces spaced in the thickness direction. The inner surface of the rim of the lens abuts against the outer face of the goggle frame, and the first and second ends of each binding cord are respectively fixedly fastened to the upper and lower ends of the outer surface of the rim of the lens.

The present invention will become clearer in light of the following detailed description of illustrative embodiments of this invention described in connection with the drawings.

DESCRIPTION OF THE DRAWINGS

The illustrative embodiments may best be described by reference to the accompanying drawings where.

DETAILED DESCRIPTION OF THE INVENTION

Figure 1:
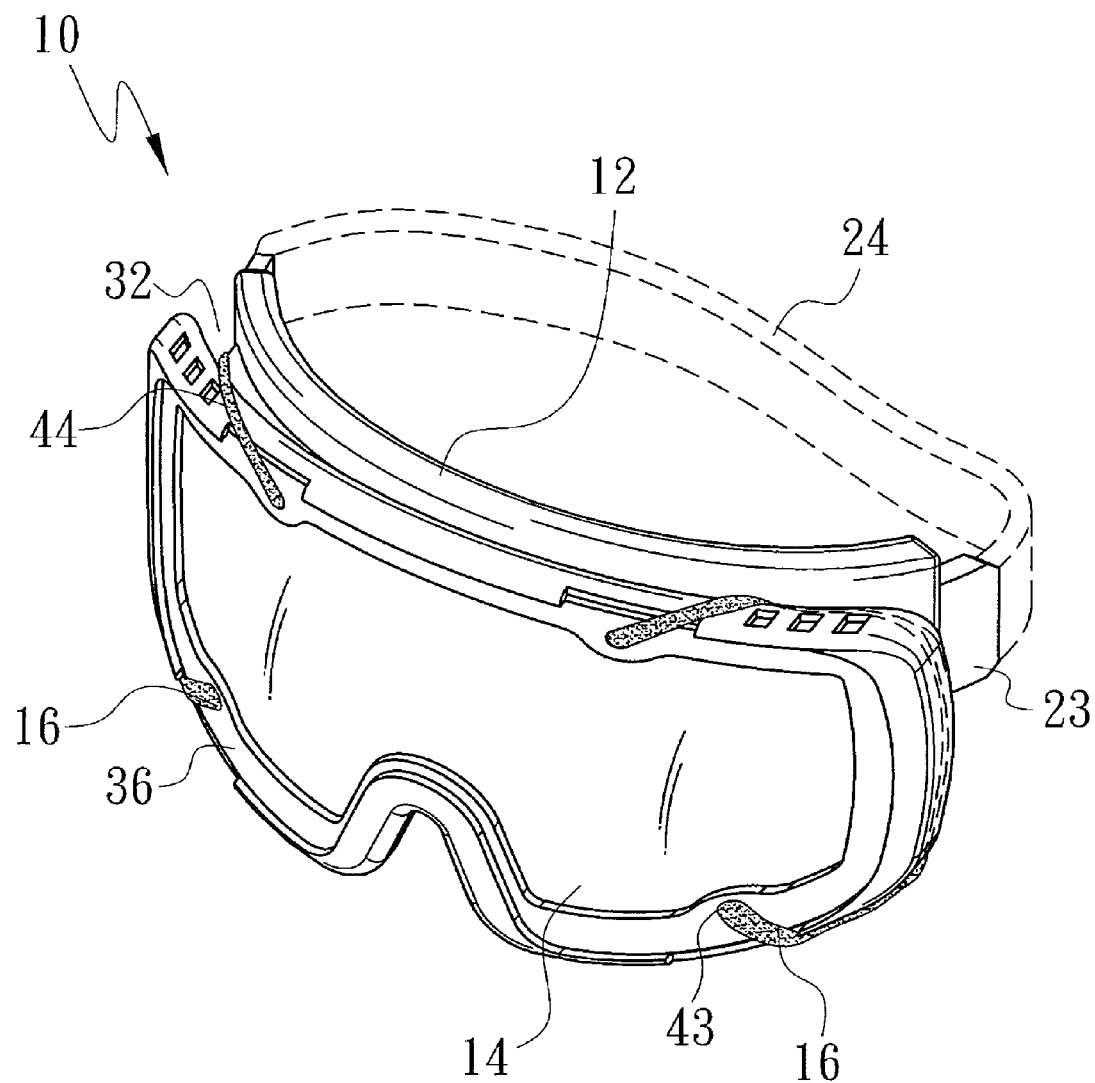
FIG. 1 is a perspective view of a combination goggle in accordance with a first embodiment of the present invention.
Figure 2:
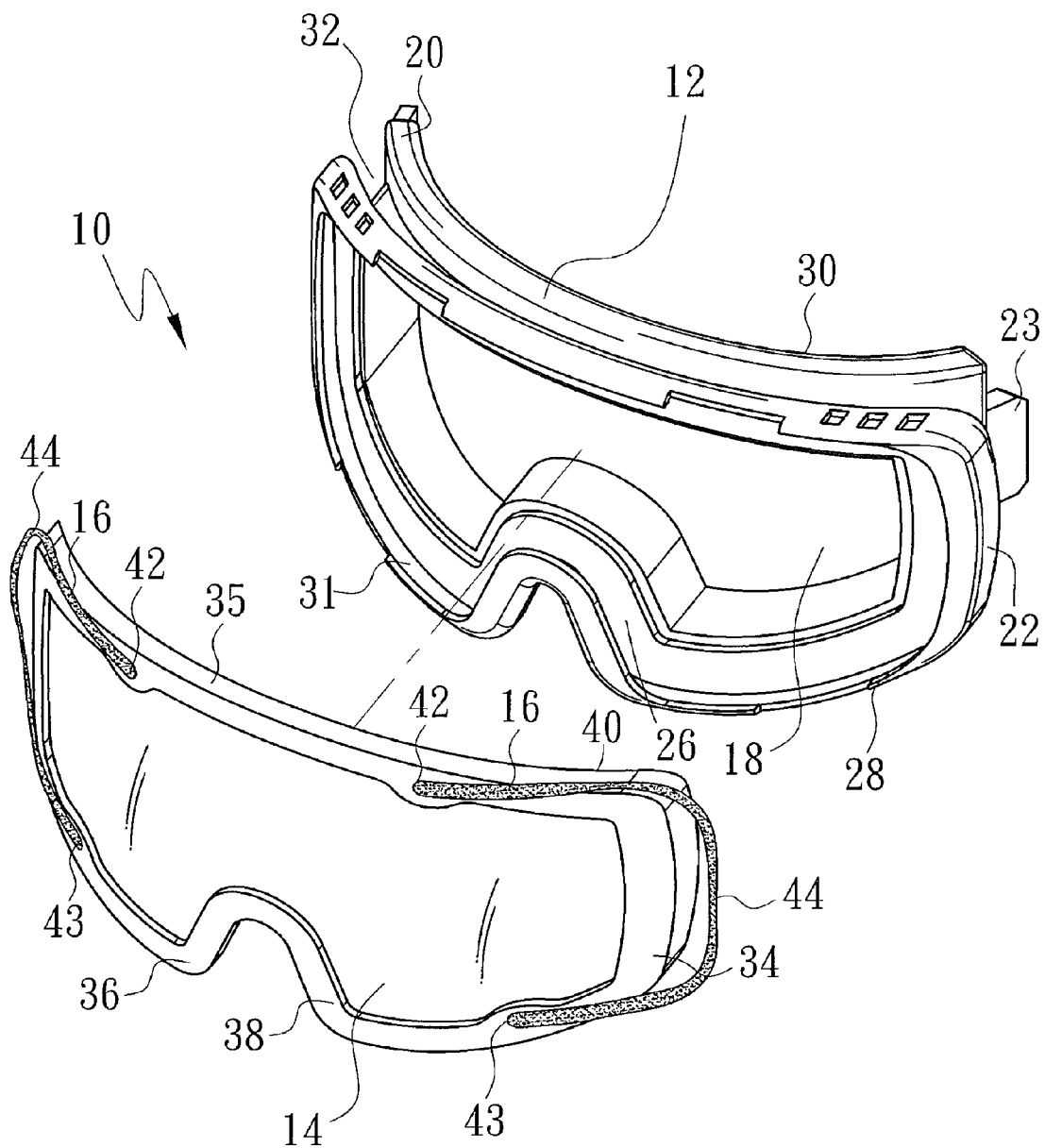
FIG. 2 shows an exploded view of the combination goggle of FIG. 1.
Figure 3:
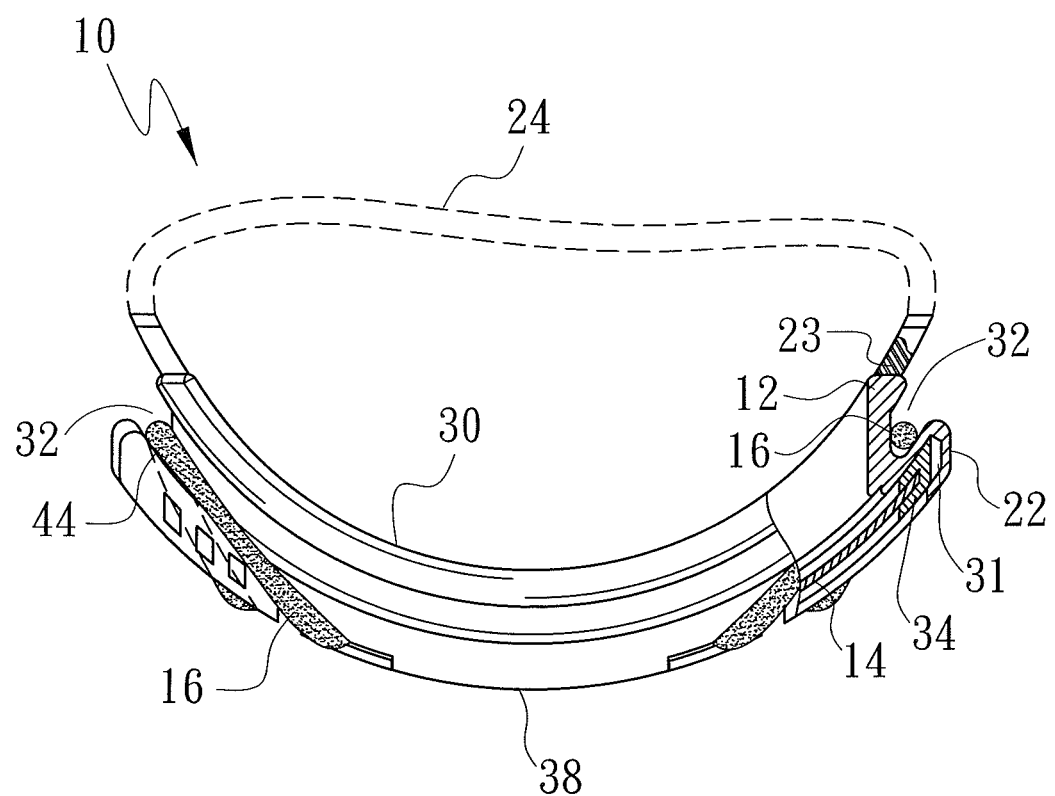
FIG. 3 shows a schematic top view of the combination goggle of FIG. 1.

A combination goggle according to the preferred teachings of the present invention is shown in FIGS. 1 through 3 of the drawings and generally designated 10. The combination goggle 10 includes a goggle frame 12, a lens 14 detachably mounted to the goggle frame 12, and two binding cords 16. The combination goggle 10 is adapted for outdoor sports application. However, it is not limited to one particular form. For example, the combination goggle 10 can be a snow goggle or sunglasses for protecting the user's eyes against light.

The goggle frame 12 can be made of plastics or rubber to support the lens 14 in place. The goggle frame 12 includes an opening 18 therein and first and second sides 20 and 22 spaced in a width direction. A lug 23 is protruded from each of the first and second sides 20 and 22 for the connection with one of two ends of a headband 24 to secure the goggle frame 12 to a head of a user. A bridge 26 is formed at a middle of a lower end of the goggle frame 12 and upwardly curved for resting on the user's nose. The goggle frame 12 further includes outer and inner faces 28 and 30 opposed in a thickness direction perpendicular to the width direction (the face facing the headband 24 is defined as the inner face 30). The goggle frame 12 further includes a recessed portion 31 formed in on the outer face 28 around the opening 18. A positioning groove 32 is provided in each of the first and second sides 20 and 22 and is located between the outer and inner faces 28 and 30 in the thickness direction. In this embodiment, each positioning groove 32 is adjacent to an outer side of one of the lugs 23.

The lens 14 is a single piece lens and has a rim 34 extending around a periphery thereof and fitting the recessed portion 31 in shape and size. Thus, the rim 34 of the lens 14 can be press-fitted into the recessed portion 31 of the goggle frame 12. The rim 34 includes upper and lower ends 35 and 36 spaced in a vertical direction perpendicular to the width and thickness directions. The rim 34 further includes outer and inner surfaces 38 and 40 opposed in the thickness direction, and the inner surface 40 of the rim 34 faces the outer face 28 of the goggle frame 12.

Each binding cord 16 is an elastic or flexible cord member and includes a first end 42, a second end 43, and a middle section 44 intermediate the first and second ends 42 and 43. The two binding cords 16 are respectively arranged on the rim 34 at two sides and kept apart from each other. The first and second ends 42 and 43 of each binding cord 16 is respectively fastened to the upper and lower ends 35 and 36 of the outer surface 38 of the rim 34 of the lens 14, and the middle section 44 of each binding cord 16 suspends outside the lens 14 for fastening to one of the positioning grooves 32 of the goggle frame 12. In this embodiment, the first and second ends 42 and 43 of each binding cord 16 are formed integral with the outer surface 38 of the rim 34. Alternatively, the first and second ends 42 and 43 of each binding cord 16 can be tied to the outer surface 38 of the rim 34, or fastened thereto by a conventional fastening technique.

During installation of the lens 14, aim the inner surface 40 of the rim 34 of the lens 14 at the outer face 28 of the goggle frame 12, and then press-fit the rim 34 into the recessed portion 31 of the goggle frame 12 to keep the two binding cords 16 in proximity to the first and second sides 20 and 22 of the goggle frame 12 respectively, and then engage the middle section 44 of each binding cord 16 in an associated positioning groove 32 so that the elasticity of the binding cords 16 secure the lens 14 to the goggle frame 12 firmly. When wishing to remove the lens 14 from the goggle frame 12, the middle section 44 of each binding cord 16 can be detached from the associated positioning groove 32 for allowing removal of the lens 14 from the goggle frame 12 directly. Further, the length of the middle section 44 of each binding cord 16 can be predetermined, or adjustable.

Based on the structural design of the combination goggle 10, it is not necessary to provide male and female fastening means at the lens 14 and the goggle frame 12 for fastening. The invention facilitates mounting and dismounting of the lens 14 and the goggle frame 12, prolonging the service life of the combination goggle 10.

Figure 4:
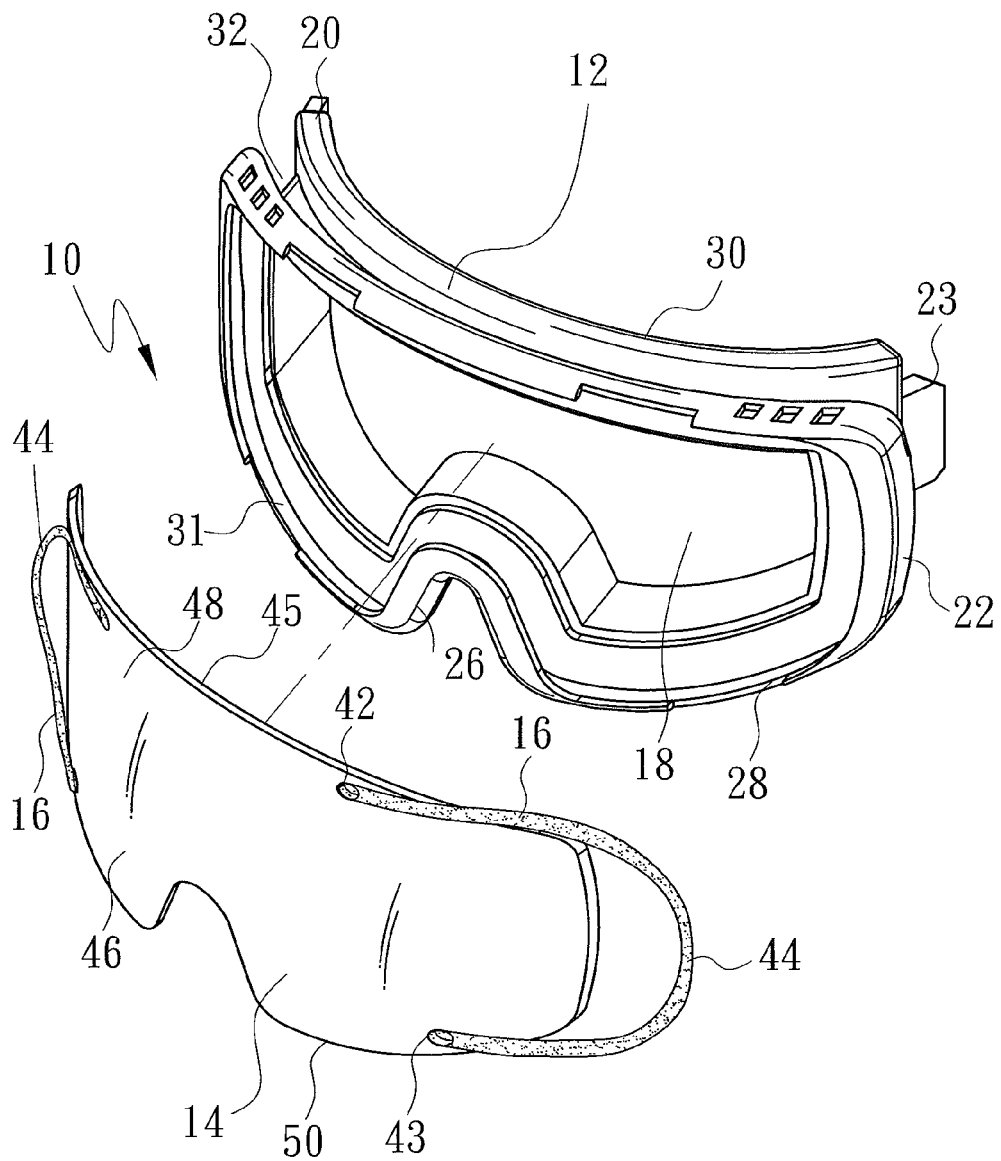
FIG. 4 is an exploded view of a combination goggle in accordance with a second embodiment of the present invention.

FIG. 4 illustrates a combination goggle 10 in accordance with a second embodiment of the present invention. According to this second embodiment, the lens 14 is a rimless lens without the aforesaid rim 34. The lens 14 includes an inner surface 45 facing the outer face 28 of the goggle frame 12 and can be press-fitted into the recessed portion 31 of the goggle frame 12. The two binding cords 16 are arranged at two sides of an outer surface 46 of the lens 14 and kept apart from each other. Further, the first and second ends 42 and 43 of each binding cord 16 are respectively affixed to upper and lower ends 48 and 50 of the outer surface 46 of the lens 14. The middle section 44 of each binding cord 16 can be engaged in an associated positioning groove 32 so that the elasticity of the binding cords 16 secure the lens 14 to the goggle frame 12 firmly.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

The invention claimed is:

1. A combination goggle, comprising:
a goggle frame including first and second sides spaced in a width direction, with the goggle frame further including outer and inner faces opposed in a thickness direction perpendicular to the width direction, with a positioning groove provided in each of the first and second sides of the goggle frame and located between the outer and inner faces of the goggle frame in the thickness direction;
a lens including outer and inner surfaces opposed in the thickness direction, with the inner surface of the lens facing and abutting against the outer face of the goggle frame; and
two binding cords respectively arranged on two sides of the lens, with each of the two binding cords including a first end, a second end, and a middle section intermediate the first and second ends, with the first and second ends of each the two binding cords being fixedly fastened to the lens, with the middle section of each of the two binding cords being detachably engaged to one of the positioning grooves of the goggle frame for fastening the lens to the goggle frame.

2. The combination goggle according to in claim 1, with the lens further including upper and lower ends spaced in a vertical direction perpendicular to the width and thickness directions, with the two binding cords arranged on the two sides of the outer surface of the lens, and with the first and second ends of each of the two binding cords respectively fixedly fastened to the upper and lower ends of the outer surface of the lens.

3. The combination goggle according to claim 2, with the goggle frame further including a lug protruded from each of the first and second sides of the goggle frame for the connection with one of two ends of a headband, and with each positioning groove being adjacent to an outer side of one of the lugs.

4. A combination goggle, comprising:
a goggle frame including first and second sides spaced in a width direction, with the goggle frame further including outer and inner faces opposed in a thickness direction perpendicular to the width direction, with a positioning groove provided in each of the first and second sides of the goggle frame;
a lens including a rim extending around a periphery thereof, with the rim including outer and inner surfaces spaced in the thickness direction, with the inner surface of the rim of the lens abutting against the outer face of the goggle frame; and
two binding cords respectively arranged on two sides of the lens, with each of the two binding cords including a first end, a second end, and a middle section intermediate the first and second ends, with the first and second ends of each the two binding cords being fixedly fastened to the lens, with the middle section of each of the two binding cords being detachably engaged to one of the positioning grooves of the goggle frame for fastening the lens to the goggle frame.

5. The combination goggle according to in claim 4, with each positioning groove located between the outer and inner faces of the goggle frame in the thickness direction, with the rim further including upper and lower ends spaced in a vertical direction perpendicular to the width and thickness directions, with the two binding cords arranged on the two sides of the outer surface of the rim of the lens, and with the first and second ends of each of the two binding cords respectively fastened to the upper and lower ends of the outer surface of the rim of the lens.

6. The combination goggle according to claim 5, with the goggle frame further including a lug protruded from each of the first and second sides of the goggle frame for the connection with one of two ends of a headband, and with each positioning groove being adjacent to an outer side of one of the lugs.

7. The combination goggle according to claim 6, with the goggle frame further including an opening therein and a recessed portion located on the outer face around the opening, and with the rim of the lens fitted in the recessed portion of the goggle frame.

\* \* \* \* \*